US010849521B2

(12) United States Patent
Highsmith et al.

(10) Patent No.: US 10,849,521 B2
(45) Date of Patent: Dec. 1, 2020

(54) MULTI-LAYERED CATHETER SHAFT CONSTRUCTION WITH EMBEDDED SINGLE AXIAL SENSORS, AND RELATED METHODS

(71) Applicant: BIOSENSE WEBSTER (ISRAEL) LTD., Yokneam (IL)

(72) Inventors: Debby E. Highsmith, Laguna Niguel, CA (US); Meir Bar-Tal, Haifa (IL); Ariel Garcia, Monrovia, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 1256 days.

(21) Appl. No.: 14/757,672

(22) Filed: Dec. 23, 2015

(65) Prior Publication Data

US 2017/0181653 A1 Jun. 29, 2017

(51) Int. Cl.
*A61B 5/05* (2006.01)
*A61M 25/16* (2006.01)
(Continued)

(52) U.S. Cl.
CPC .............. *A61B 5/042* (2013.01); *A61B 5/062* (2013.01); *A61B 5/065* (2013.01); *A61B 5/6851* (2013.01);
(Continued)

(58) Field of Classification Search
CPC .............. A61B 5/042; A61B 2562/043; A61M 25/0012; A61M 25/005; A61M 25/0127
See application file for complete search history.

(56) References Cited

U.S. PATENT DOCUMENTS 4,815,478 A 3/1989 Buchbinder et al.
RE34,502 E 1/1994 Webster, Jr.
(Continued)

FOREIGN PATENT DOCUMENTS

EP 1 457 226 A2 9/2004
EP 1 562 665 A2 8/2005
(Continued)

OTHER PUBLICATIONS

Notification of Reasons for Refusal (English Translation Only) for Japanese Patent Application No. 2011-288664, dated Nov. 24, 2015, 5 pages.
(Continued)

*Primary Examiner* — Lee S Cohen
*Assistant Examiner* — Erin M Cardinal
(74) *Attorney, Agent, or Firm* — Lewis Roca Rothgerber Christie LLP

(57) ABSTRACT

A catheter is provided with improved position and/or location sensing with the use of single axis sensors that are mounted directly along a length or portion of the catheter whose position/location is of interest. The magnetic based, single axis sensors are provided on a single axis sensor (SAS) assembly, which can be linear or nonlinear as needed. A catheter of the present invention thus includes a catheter body and a distal member of a particular 2D or 3D configuration that is provided by a support member on which at least one, if not at least three single axis sensors, are mounted serially along a length of the support member. In one embodiment, the magnetic-based sensor assembly including at least one coil member that is wrapped on the support member, wherein the coil member is connected via a joint region to a respective cable member adapted to transmit a signal providing location information from the coil member to a mapping and localization system. The joint region
(Continued)

advantageously provides strain relief adaptations to the at least one coil member and the respective cable member from detaching.

20 Claims, 6 Drawing Sheets

(51) Int. Cl.
| | | |
|---|---|---|
| A61B 5/042 | (2006.01) | |
| B29C 48/10 | (2019.01) | |
| A61B 5/06 | (2006.01) | |
| A61B 5/00 | (2006.01) | |
| A61M 25/01 | (2006.01) | |
| A61M 25/00 | (2006.01) | |
| B29C 45/14 | (2006.01) | |
| B29C 63/00 | (2006.01) | |
| B29C 63/18 | (2006.01) | |
| B29K 21/00 | (2006.01) | |
| B29K 63/00 | (2006.01) | |
| B29K 75/00 | (2006.01) | |
| B29L 31/00 | (2006.01) | |

(52) U.S. Cl.
CPC ...... *A61M 25/005* (2013.01); *A61M 25/0012* (2013.01); *A61M 25/0082* (2013.01); *A61M 25/0127* (2013.01); *B29C 45/14622* (2013.01); *B29C 48/10* (2019.02); *B29C 63/0069* (2013.01); *B29C 63/18* (2013.01); *A61B 2562/043* (2013.01); *A61M 25/0045* (2013.01); *A61M 2025/0166* (2013.01); *B29K 2021/003* (2013.01); *B29K 2063/00* (2013.01); *B29K 2075/00* (2013.01); *B29L 2031/7542* (2013.01)

(56) References Cited

U.S. PATENT DOCUMENTS

| | | |
|---|---|---|
| 5,275,151 A | 1/1994 | Shockey et al. |
| 5,391,199 A | 2/1995 | Ben-Haim |
| 5,395,329 A | 3/1995 | Fleischhackor et al. |
| 5,443,489 A | 8/1995 | Ben-Haim |
| 5,645,065 A | 7/1997 | Shapiro et al. |
| 5,656,029 A | 8/1997 | Imran et al. |
| 5,755,687 A * | 5/1998 | Donlon ............ A61B 17/12022 600/18 |
| 5,891,088 A | 4/1999 | Thompson et al. |
| 5,997,473 A | 12/1999 | Taniguchi |
| 6,123,699 A | 9/2000 | Webster, Jr. |
| 6,171,277 B1 | 1/2001 | Ponzi |
| 6,183,463 B1 | 2/2001 | Webster, Jr. |
| 6,375,606 B1 * | 4/2002 | Garibaldi ......... A61B 17/12022 600/12 |
| 6,484,118 B1 | 11/2002 | Govari |
| 6,491,681 B1 | 12/2002 | Kunis et al. |
| 6,500,129 B1 | 12/2002 | Mahurkar |
| 6,554,794 B1 | 4/2003 | Mueller et al. |
| 6,574,492 B1 | 6/2003 | Ben-Haim et al. |
| 6,690,963 B2 | 2/2004 | Ben-Haim et al. |
| 6,788,967 B2 | 9/2004 | Ben-Haim et al. |
| 6,847,837 B1 * | 1/2005 | Melzer ................. A61B 5/055 324/307 |
| 6,892,090 B2 | 5/2005 | Verard et al. |
| 6,961,602 B2 | 11/2005 | Fuimaono et al. |
| 7,174,202 B2 | 2/2007 | Bladen et al. |
| 7,274,957 B2 | 9/2007 | Drysen |
| 7,615,044 B2 | 11/2009 | Scheibe et al. |
| 7,931,616 B2 | 4/2011 | Selkee |
| 8,118,775 B2 | 2/2012 | Grunewald et al. |
| 8,382,662 B2 | 2/2013 | Soper et al. |
| 8,529,505 B2 | 9/2013 | Grunewald et al. |
| 8,700,133 B2 | 4/2014 | Hann |
| 8,792,962 B2 | 7/2014 | Esguerra et al. |
| 8,805,472 B2 | 8/2014 | Iglesias |
| 8,880,147 B2 | 11/2014 | Tegg et al. |
| 8,926,528 B2 | 1/2015 | Govari et al. |
| 8,936,583 B2 | 1/2015 | Holzbauer et al. |
| 2003/0028096 A1 | 2/2003 | Niwa et al. |
| 2003/0160721 A1 | 8/2003 | Gilboa et al. |
| 2004/0097965 A1 * | 5/2004 | Gardeski .......... A61M 25/0021 606/129 |
| 2005/0274425 A1 | 12/2005 | Ostrander et al. |
| 2007/0164900 A1 | 7/2007 | Schneider et al. |
| 2008/0255540 A1 | 10/2008 | Selkee |
| 2009/0005754 A1 | 1/2009 | Soetermans |
| 2009/0192412 A1 | 7/2009 | Sela et al. |
| 2010/0036285 A1 | 2/2010 | Govari |
| 2010/0069834 A1 | 3/2010 | Schultz |
| 2010/0168827 A1 | 7/2010 | Schultz |
| 2010/0222664 A1 | 9/2010 | Lemon et al. |
| 2011/0054287 A1 | 3/2011 | Schultz |
| 2011/0077498 A1 * | 3/2011 | McDaniel .......... A61B 18/1492 600/374 |
| 2012/0143088 A1 | 6/2012 | Schultz |
| 2012/0172703 A1 * | 7/2012 | Esguerra ................ A61B 5/062 600/409 |
| 2012/0172842 A1 * | 7/2012 | Sela ..................... A61B 5/0402 604/528 |
| 2014/0228838 A1 | 8/2014 | Kirschenman |
| 2014/0275957 A1 | 9/2014 | Lupotti |
| 2015/0190092 A1 * | 7/2015 | Mori .................... A61B 5/6852 600/374 |

FOREIGN PATENT DOCUMENTS

| | | |
|---|---|---|
| EP | 2 151 209 A2 | 2/2010 |
| EP | 2 165 730 A1 | 3/2010 |
| EP | 2 301 617 A1 | 3/2011 |
| EP | 2 460 558 A1 | 6/2012 |
| EP | 2 897 524 A1 | 7/2015 |
| JP | 2010-36040 | 2/2010 |
| WO | WO 96/34652 A1 | 11/1996 |
| WO | WO 2007/130720 A1 | 11/2007 |

OTHER PUBLICATIONS

Extended European Search Report dated Feb. 14, 2012, for EP 11191759.7 (3 pages).
Partial European Search Report dated Jun. 25, 2012 for EP 11196031 (6 pages).
Extended European Search Report dated Sep. 17, 2012 for EP 11196031 (12 pages).
European Patent Office Search Report dated May 26, 2017 for EP Application No. 16206180.8, 9 pages.

* cited by examiner

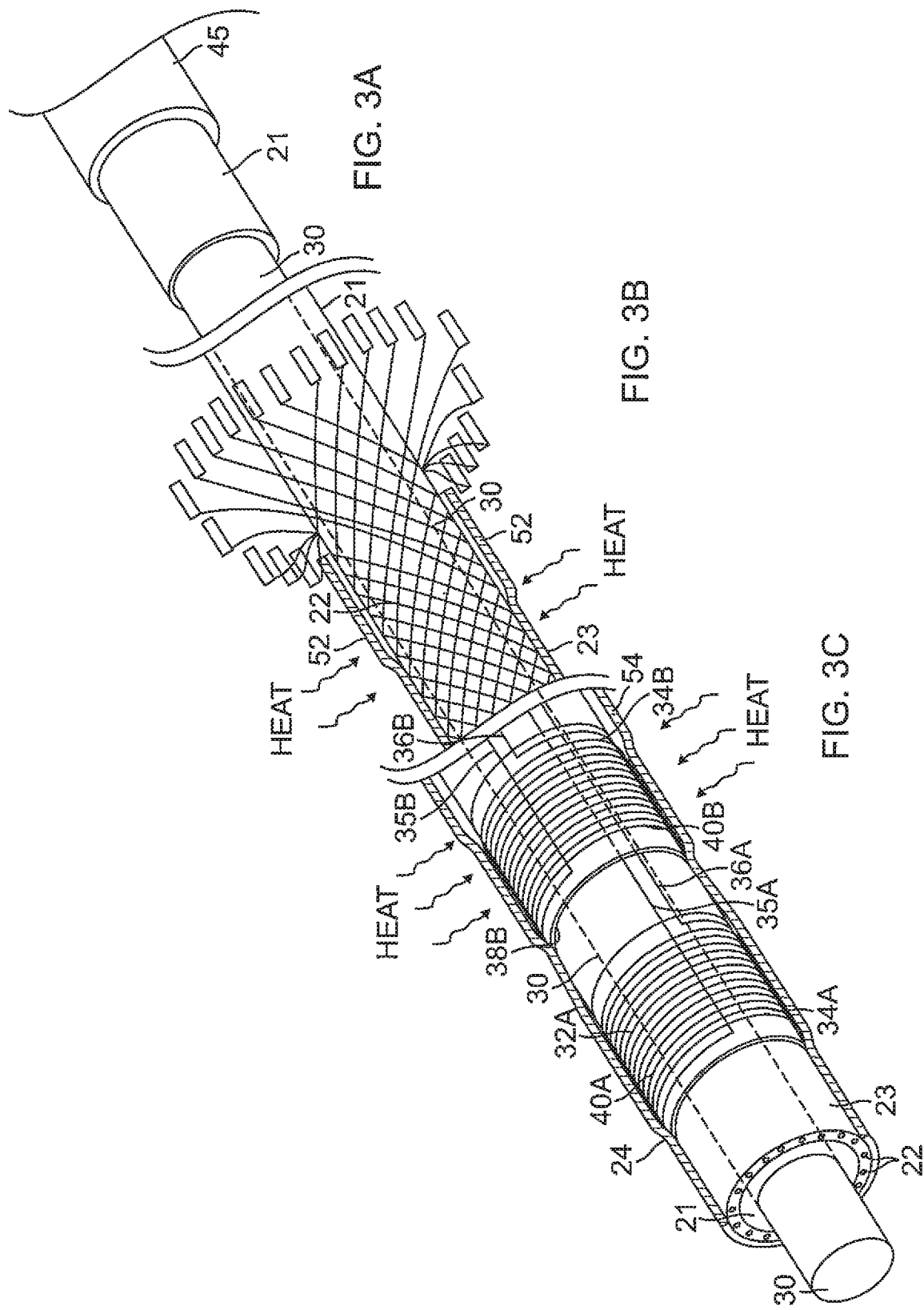

US 10,849,521 B2

MULTI-LAYERED CATHETER SHAFT CONSTRUCTION WITH EMBEDDED SINGLE AXIAL SENSORS, AND RELATED METHODS

FIELD OF INVENTION

This invention relates to a catheter, in particular, a catheter whose shaft portion is adapted for position sensing to provide visualization of the shaft portion.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a distal mapping and/or ablation electrode assembly that is adapted to measure activity within a pulmonary vein, coronary sinus or other tubular structure about the inner circumference of the structure. For visualization of a distal electrode assembly, one or more single Axis Sensors (SAS) may be mounted on a support member of the distal electrode assembly, as described in U.S. Pat. No. 8,792,962, issued Jul. 29, 2014, entire content of which is incorporated herein by reference.

Visualization of a catheter shaft proximal of a distal electrode assembly, including any portion of the catheter shaft, such as a proximal portion or a distal deflectable portion, may also be helpful to an operator during mapping and/or ablation procedures. It is therefore desirable for a catheter shaft to enable visualization, and especially where such visualization can be accomplished for catheter shafts with smaller diameters without increasing shaft diameter.

SUMMARY OF THE INVENTION

The present invention is directed to a catheter with improved position and/or location sensing with the use of magnetic-based, single axis sensors (SAS) that are embedded in a multi-layered sidewall of catheter tubing to enable position sensing and visualization of the catheter tubing.

In some embodiments of the present invention, a catheter comprises an elongated body having a multi-layered portion with a magnetic-based sensor subassembly, a control handle proximal of the elongated body, and a distal section distal of the elongated body, the distal section having an electrode. Advantageously, the multi-layered portion has a first layer, a braided mesh over the first layer, and a second layer, the first layer defining an inner lumen, the second layer having a reflowed construction over the braided mesh and the first layer, and the first and second layers being of similar thermoplastic materials. Mounted on top of the second layer is the magnetic-based sensor subassembly with a first wire sensor with a first wire coil portion wounded on the second layer at a first location, and a first wire distal portion and a first wire proximal portion extending longitudinally toward a proximal end of the elongated body.

In detailed embodiments, the magnetic-based sensor subassembly has a second wire sensor with a second wire coil portion, a second wire distal portion and a second wire proximal portion, the second wire coil portion wounded on the second layer at a second location proximal of the first location, the second wire distal portion and the second wire proximal portion extending longitudinally toward a proximal end of the elongated body.

In detailed embodiments, the first wire distal portion and the first proximal portion of the first wire sensor pass between the second layer and the second wire coil portion.

In detailed embodiments, the magnetic-based sensor assembly includes a nonconductive sleeve fitted on the second layer separating the first wire distal and proximal portions from contacting the second wire coil portion.

In other embodiments, the magnetic-based sensor assembly has a third wire sensor with a third wire coil portion, a third wire distal portion and a third wire proximal portion, the third wire coil portion being at a third location on the second layer of the elongated body, the third location being proximal of the first and second locations, the third wire distal portion and the third wire proximal portion extending longitudinally toward a proximal end of the elongated body.

In detailed embodiments, the first distal portion and the second proximal portion of the second wire sensor pass between the second layer and the second wire coil portion at the second location and between the second layer and the third wire coil portion at the third location.

In detailed embodiments, the magnetic-based sensor assembly includes a nonconductive sleeve fitted on the second layer separating the first and second wire distal and proximal portions from contacting the third wire coil portion.

In other embodiments, the elongated body has a third layer covering at least the multi-portion of the elongated body to seal the magnetic-based sensor subassembly.

In some embodiments of the present invention, a catheter comprises an elongated body having a multi-layered portion with a magnetic-based sensor subassembly, a control handle proximal of the elongated body, and a distal section distal of the elongated body, the distal section having an electrode. Advantageously, the multi-layered portion has a first layer with multiple lumens, a braided mesh over the first layer, and a second layer, the first layer defining an inner lumen, the second layer having a reflowed construction over the braided mesh and the first layer, and the first and second layers being of similar thermoplastic materials. Mounted on top of the second layer is the magnetic-based sensor subassembly with a first wire sensor with a first wire coil portion wounded on the second layer at a first location, and a first wire distal portion and a first wire proximal portion extending longitudinally toward a proximal end of the elongated body.

In detailed embodiments, the first wire distal portion and the second wire proximal portion pass through respective through-holes formed in the multi-layered portion in communication with the inner lumen, wherein the first wire distal portion and the first wire proximal portion extend longitudinally toward a proximal end of the elongated body through the inner lumen.

The present invention is also directed to a method of method of manufacturing a catheter tubing with improved position and/or location sensing with the use of magnetic-based, single axis sensors (SAS) that are embedded in a multi-layered sidewall of catheter tubing to enable position sensing and visualization of the catheter tubing.

In some embodiments, the method comprises extruding the first layer, placing the braided mesh on the first layer, placing a first heat shrink tubing as the second layer over the braided mesh and the first layer, and heating the first heat shrink tubing to reflow the second layer over the braided mesh and the first layer.

In some embodiments, the method further comprises placing a second heat shrink tubing over at least the first coil portion, and heating the second heat shrink tubing to form a seal over at least the first coil portion.

In other embodiments, method of manufacturing comprising extruding the first layer, placing the braided mesh on the first layer, placing a first heat shrink tubing as the second layer over the braided mesh and the first layer, heating the first heat shrink tubing to a temperature within the overlapping temperature ranges of the first and second thermoplastic materials, and wrapping the first wire sensor on the second layer.

In some embodiments, the method further comprises supporting the first layer with a mandrel that remains with the first layer during at least the wrapping the first wire sensor on the second layer.

In yet other embodiments, a method of manufacturing comprises extruding the first layer, placing the braided mesh on the first layer, placing a first heat shrink tubing over the braided mesh and the first layer, heating the first heat shrink tubing to a temperature to sufficiently melt the first and second layers to adhere to each other, placing a respective sleeve on the second layer for each wire sensor, and wrapping each wire sensor on the second layer with a mandrel supporting the first layer, the braided mesh and the second layer.

In detailed embodiments, the method further comprises placing a second heat shrink tubing as a third layer over each wire sensor, and heating the second heat shrink tubing to seal each wire sensor on the elongated body.

In detailed embodiments, the method further comprises injecting epoxy through the second heat shrink tubing to encase each wire sensor.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 3A, FIG. 3B and FIG. 3C are side views of a catheter tubing of FIG. 2A, during manufacturing, in accordance one embodiment of the present invention.

DETAILED DESCRIPTION OF THE INVENTION

Figure 1:
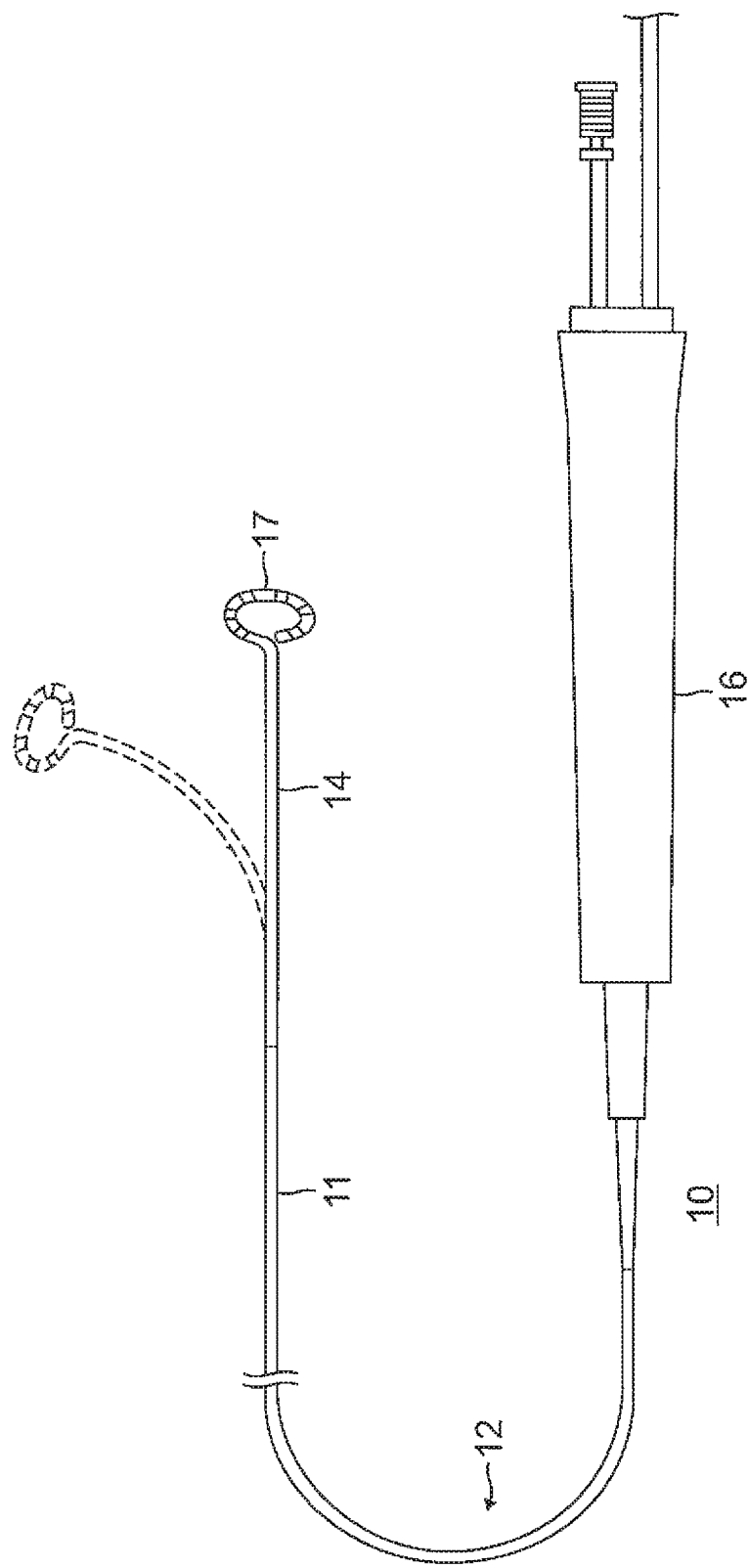
FIG. 1 is a top plan view of a catheter of the present invention, in accordance with one embodiment.

Referring to FIG. 1, the present invention is directed to a catheter 10 with a multi-layered catheter shaft portion 11 adapted for position sensing for visualization of the shaft portion 11. The shaft portion 11 may be part of an elongated catheter tubing, for example, an elongated catheter body 12, or a shorter deflection portion 14 distal of the catheter body 12, wherein position sensing is accomplished by one or more single axis sensors (SAS) encased in the shaft portion 11 which is constructed of multiple layers of similar materials, for example, with similar melting temperatures to promote a composite construction and adherence of the layers.

Proximal of the catheter body 12 is a control handle 16 with mechanisms that are manipulated by a user to accomplish, for example, bi-directional deflection of the deflection section 14. Distal of the deflection portion 14 is a distal electrode assembly 17 with one or more electrodes arranged in a 2-D or 3-D configuration.

Figure 2A:
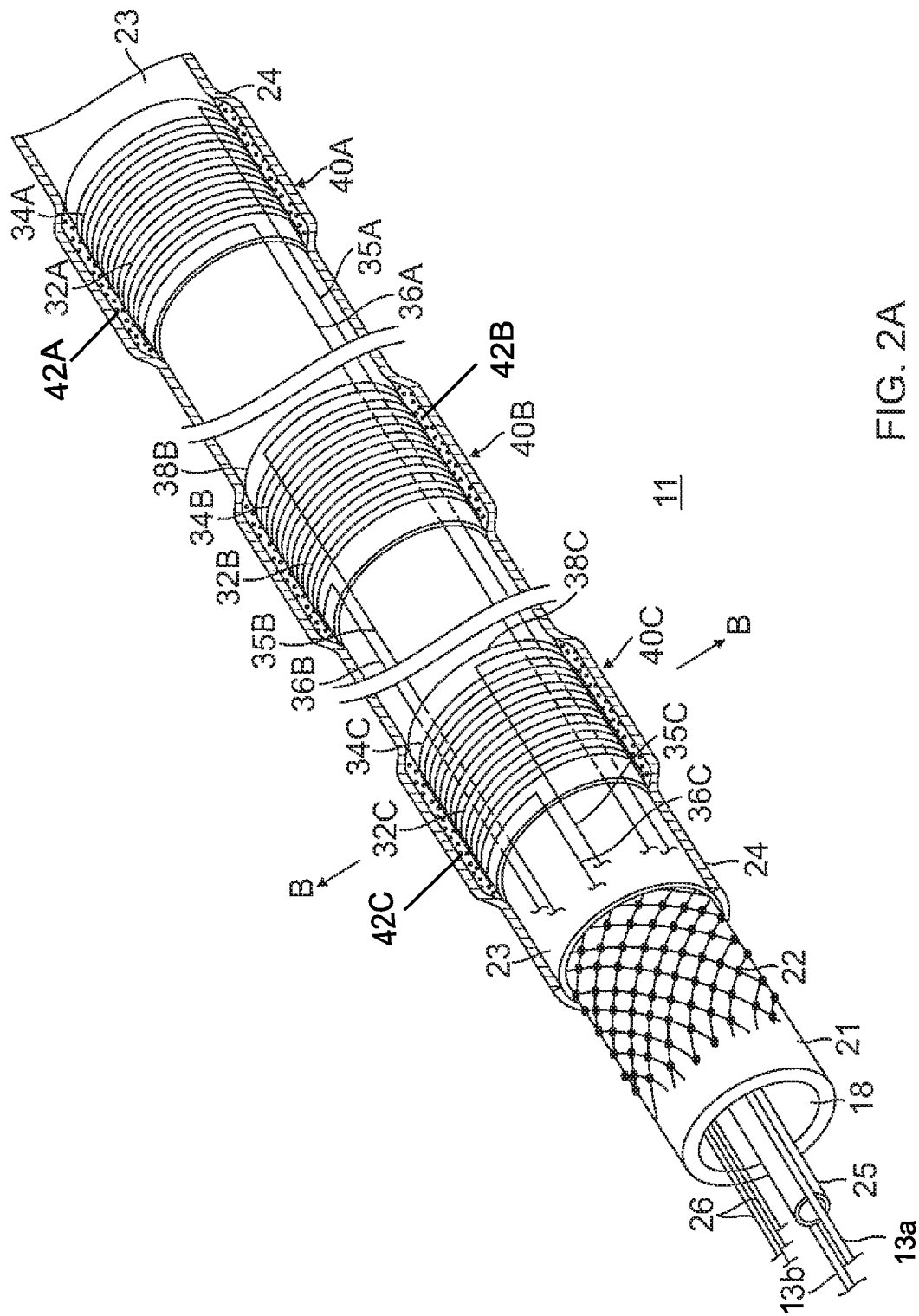
FIG. 2A is a side view of a catheter tubing of the catheter of FIG. 1, with parts broken away.
Figure 2B:
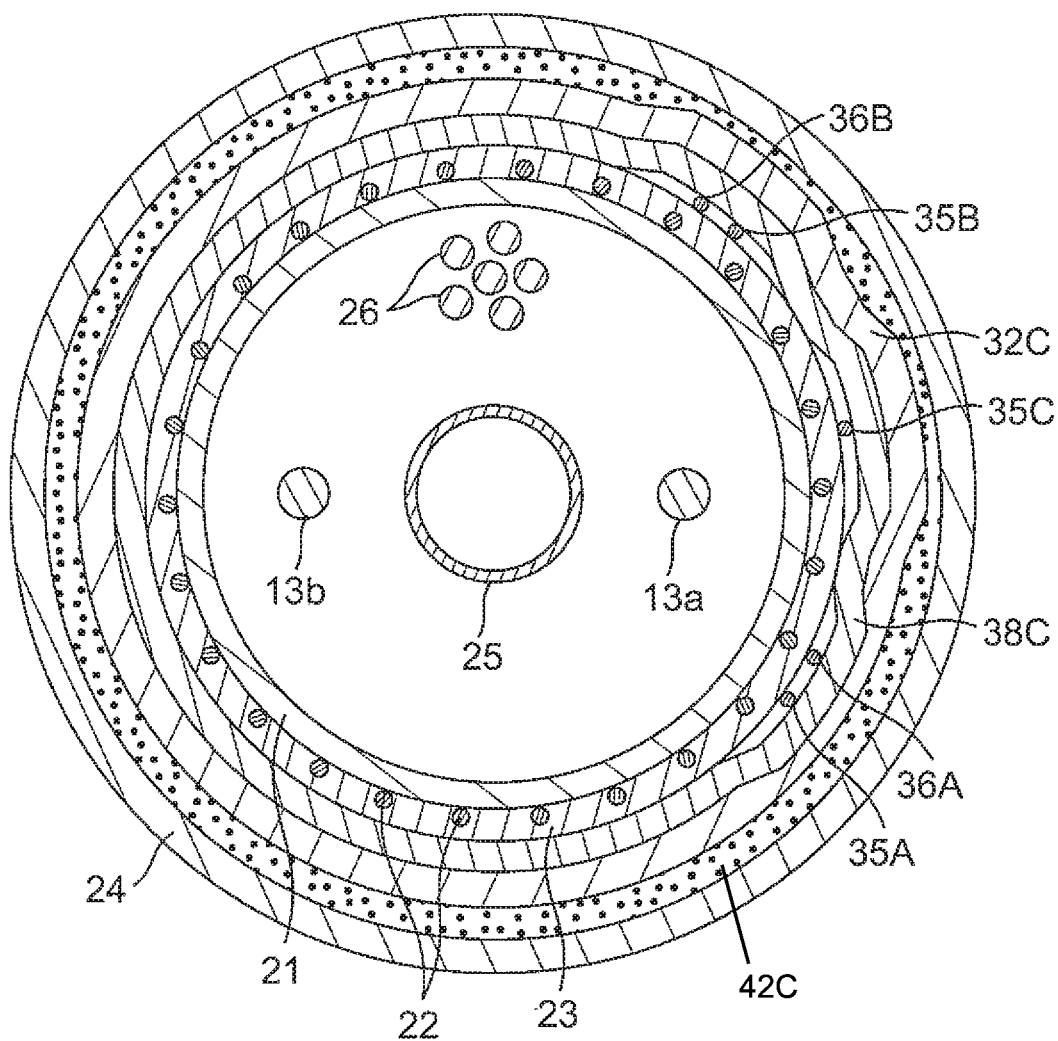
FIG. 2B is an end cross-sectional view of the catheter tubing of FIG. 2A, taken along line B-B.

With reference to FIGS. 2A and 2B, the catheter body 12 comprises a single, central or axial lumen 18. The catheter body 12 is flexible, i.e., bendable, but substantially non-compressible along its length. As part of the catheter body 12, the shaft portion 11 and the catheter body 12 have a similar construction comprising an inner wall or first layer 21 of a thermoplastic material, an imbedded braided mesh 22, and a thin wall or second layer 23 of a thermoplastic material surrounding the braided mesh 22 and the first layer 21. Suitable thermoplastic materials include, for example, thermoplastic elastomers (TPEs) and thermoplastic polyurethanes (TPUs), such as PELLETHANE or PEBAX, where PEBAX has a melting temperature ranging between about 272° F. (133° C.) and 345° F. (174° C.) and PELLETHANE has a melting temperature ranging between about 360° F. (182° C.) and 441° F. (227° C.). In some embodiments, the same thermoplastic material is used for the first layer 21 and the second layer 23. In some embodiments, the first layer 21 comprises a first thermoplastic material and the second layer 23 comprises a second thermoplastic material similar to the first thermoplastic material. Similar thermoplastic materials are understood herein to be thermoplastic materials have melting temperatures such that heating and reflowing of at least one layer promote and enable bonding and adherence of one layer to the other layer. In some embodiments, similar thermoplastic materials have melting temperature ranges that are similar, which include thermoplastic materials with melting temperature ranges that overlap by or have in common at least about one degree in Fahrenheit (one degree in Celsius), preferably about five degrees in Fahrenheit (three degrees in Celsius), and more preferably about ten degrees in Fahrenheit (five degrees in Celsius). It is understood that "similar" can refer to the same chemical materials having the same melting temperatures, and to different chemical materials having different chemical make-ups but similar melting temperature ranges as defined herein. In some embodiments, the "different chemical materials" might include, for example, similar polymer backbones but different pendant groups, or different polymer backbones.

The imbedded braided mesh 22 of stainless steel or the like is provided to increase torsional stiffness of the catheter body 12 so that when the control handle 16 is rotated the length of the catheter body 12 rotates in a corresponding manner. The single lumen 18 permits components passing therethrough (including, for example, irrigation tubing 25, electrode lead wires 26, puller wires 13a, 13b, etc.) to float freely within the catheter body 12. However, if desired or appropriate, the catheter body 12 may also have a multi-lumened extrusion construction.

The thin wall or second layer 23 is constructed of a second thermoplastic material which is reflowed over the braided mesh 22. With the first and second layers 21 and 23 being of the same or similar thermoplastic materials, reflowing the second layer 23 over the braided mesh 22 and the first layer 21 promotes the catheter body 12 having a composite construction and adherence of the first and second layers 21 and 23 to each other.

The first layer 21 may have an outer diameter ranging between about 0.069" and 0.073", and preferably, a diameter of about 0.071". A sidewall of the first layer 21 may have a thickness ranging between about 0.003" and 0.006", and preferably, a thickness of about 0.004".

The second layer 23 may have an outer diameter ranging between about 0.100" and 0.109", and preferably, a diameter of about 0.104". A sidewall of the second layer 23 may have a thickness ranging between about 0.002" and 0.006", and preferably, a thickness of about 0.003".

As shown in FIG. 2A, one or more linear single axis sensors (SAS) 40A, 40B and 40C forming a SAS subassembly are mounted on the bonded composite catheter shaft portion 11 as part of the catheter body 12. The SAS 40A comprises a coil 32A of multiple windings of an electrical conductor (e.g., very fine small gauge wire 34A) situated on an outer surface of the second layer 23. A distal portion 35A of the wire passes under the coil 32A and extends in a longitudinal direction toward a proximal end of the catheter shaft portion 11 and the control handle 16. A proximal portion 36A of the wire 34A also extends in the longitudinal direction toward the proximal end of the catheter shaft 11 and the control handle 16. The coil 32A may incorporate strain relief adaptations, including slack and/or windings, as disclosed in U.S. Pat. No. 8,792,962, issued Jul. 29, 2014, entire content of which is incorporated herein by reference. The SAS 40B and 40C have a similar construction, and thus similar components thereof are identified in the Figures with similar reference numbers with letter designation of B or C.

Each SAS interacts with at least one external magnetic field generated by a magnetic field generator positioned, for example, below the patient bed. Each SAS generates signals representative of the relative strengths of the field as sensed by its coil, which signals are transmitted proximally toward the control handle 16 and further to a highly accurate mapping system, such as CARTO, CARTO XP or CARTO 3, available from Biosense Webster, to provide visualization of the shaft portion 11 and to create 3-D anatomical maps of tissue chamber or region of interest in the patient, based on location and orientation of the shaft portion 11 on which the SAS subassembly is mounted.

As shown in FIG. 2A, distal SAS 40A has wire distal portion 35A and wire proximal portion 36A, mid SAS 40B has wire distal portion 35B and wire proximal portion 36B, and proximal SAS 40C has wire distal portion 35C and wire proximal portion 36C. To insulate the wire distal and proximal portions of the more distal SAS from the more proximal SAS, a nonconductive sleeve 38 is placed and fitted on the shaft portion 11 between the second layer 23 and the coil 32, with the wire distal and proximal portions of more distal SAS passing between the sleeve 38 and the second layer 23. In the embodiment of FIG. 2A, insulating sleeve 38B is provided under the coil 32B to insulate wire portions 35A and 36A from the coil 32A, and insulating sleeve 38C (also shown in FIG. 2B) is provided under the coil 32C to insulate wire portions 35A, 36A, 35B and 36B from the coil 32C. In that regard, the sleeves 38B and 38C are shaped and sized to provide sufficient and adequate insulation surfaces on which the coils 32B and 32C may be wounded without contacting the underpassing wire portions. The wire 34 may comprise flat ribbon wires that can lie flatter against the second layer 23 for a minimized profile when passed under the sleeves 38B and 38C.

In some embodiments, each SAS includes an encapsulation coating or layer 42 encasing the coil 32, surrounding it circumferentially on the catheter shaft portion 11 (also shown in FIG. 2B). The layer 42 may be of any suitable material, including, for example, epoxy, UV glue, or the like. The encapsulation layer 42 provides a number of benefits, including protecting the coil 32 from exposure to increased temperatures during reflow process, and providing strain relief to minimize wire breakage or damage during assembly and use. For distal SAS 40A, the encapsulation layer 42A encases the coil 32A with the second layer 23. For mid and proximal SAS 40B and 40C, the encapsulating layer 42B and 42C encases the coils 32B and 32C with the sleeves 38B and 38C, respectively.

In some embodiments, the shaft portion 11 includes an outer wall or third layer 24 that extends over the SAS subassembly, if not also the length of the catheter body 12. As shown in FIG. 2A, the third layer 24 protects the coils 32A, 32B and 32C, and the wire distal and proximal portions 35A, 36A, 35B, 36B, 35C and 36C.

In construction of the catheter body 12, including the shaft portion 11, according to some embodiments of the present invention, as shown in FIG. 3A, the first layer 21 is extruded from an extruder 45 over a mandrel 30 which forms the central lumen 18 (FIG. 2A) of the shaft portion 11. As shown in FIG. 3B, the mandrel 30 (in broken lines) may remain under the extruded first layer 21 as the mesh 22 is braided over the first layer 21. As shown in FIG. 3B, the mandrel 30 may remain under the extruded first layer 21 and the braided mesh 22 as a heat shrink tubing 52 forming the second layer 23 is extruded over or otherwise fitted on the first layer 21 and braided mesh 22. The mandrel 30 may remain in the first layer 21 as heat is applied to the heat shrink tubing 52 to reflow over the braided mesh 22 and the first layer 21 in forming the second layer 23. As described above, the heated tubing 52 is reflowed so that the second thermoplastic material can seep through the braided mesh 22 and bond with the first thermoplastic material of the first layer 21. The similarity in melting temperatures of the first and second thermoplastic materials facilitates such bonding and adherence.

As shown in FIG. 3C, the distal most SAS, for example, SAS 40A is mounted first. Wire distal portion 35A of thin wire 34A is laid longitudinally on the outer surface of the second layer 23 and the thin wire 34A is coiled around the shaft portion 11, on top of the wire distal portion 35A. The remainder of the wire distal portion 35A extends proximally of the coil 32A toward a proximal end of the catheter body 12. Proximal of the coil 32, wire proximal portion 36A of the wire 34A is laid longitudinally on the outer surface of the second layer 23 also extending proximally toward a proximal end of the catheter body 12.

Before mounting the next distal SAS at a selected location proximal of the distal-most SAS 40A, for example, the mid SAS 40B, sleeve 38B is mounted over the second layer 23 and the wire distal and proximal portions 35A and 36A at the selected location. In some embodiments, the sleeve 38B may be a short heat-shrink tubing that is reflowed over the wire portions 35A and 36A, and the second layer 23. To mount the mid SAS 40B, wire distal portion 35B of thin wire 34B is laid longitudinally on the sleeve 38B, and the thin wire 34B is coiled around the shaft portion 11 over the wire distal portion 35B and the sleeve 38B (which covers and insulates the wire distal portion 35A and the wire proximal portion 36A from the coil 34B). Wire proximal portion 36B of the wire 34B is laid longitudinally on the sleeve 38B and further on the outer surface of the second layer 23 as it extends proximally toward a proximal end of the catheter body 12.

Additional SAS, including SAS 40C may be mounted in the same manner as described above for SAS 40B.

As shown in FIG. 3C, the third layer 24 may also be applied as a heat shrink tubing 54 which seals in all the components mounted and carried on the shaft portion 11. The tubing 54 is reflowed over the second layer 23, the coils 32A and 32B, the sleeves 38B, and the wire portions 35A, 36A, 35A, 35B. The encapsulation coatings or layers 42A, 42B and 42C (see FIG. 2B) may applied to the coils before the tubing 54 is fitted over the coils, or they may be applied via syringe injection through the heat shrink-tubing 54 before it is reflowed into forming the third layer 24. The third layer 24 is constructed of a third thermoplastic material which may be the same as the first and/or second thermoplastic material, or be similar to the first and/or second thermoplastic material, in promoting bonding and adherence of one or more layers of the multi-layer construction of the shaft portion 11.

As shown in FIG. 3A, FIGS. 3B and 3C, the mandrel 30 may remain in the first layer 21 during at least the winding of the coil of the one or more SASes on the second layer 23, and if not also during the application/reflow of the third layer 24, so as to maintain the structural shape of the shaft portion 11 and the central lumen 18. It is understood that the mandrel supporting the structural shape need not be the same mandrel used throughout the manufacturing of the shaft portion 11 but that the mandrel 30 may be removed and replaced with one or more mandrels as suitable or appropriate during the winding of the coil of the one or more SAS on the second layer 23, and/or any of the reflow stages during manufacturing of the shaft portion 11.

It is understood that FIG. 3A, FIG. 3B and FIG. 3C are representative illustrations demonstrating various steps of constructing a multi-layered catheter body with an embedded SAS subassembly within the side wall of the catheter body, in accordance with some embodiments of the present invention. Although the steps illustrated may be performed in an assembly line fashion, with progression from FIG. 3A, to FIG. 3B to FIG. 3C, the steps may also be performed discretely, in different assembly lines, by different machinery and/or at different locations. For example, while FIG. 3B illustrates the reflowing of the heat shrink tubing 52 at one location on the catheter body as occurring simultaneously with the application of the braided mesh 22 at another location on the catheter body, it is understood that the application of the braided mesh may be completed entirely along the length of the catheter body 12 before the heat shrink tubing 52 is fitted over the catheter body 12 and before heat is applied to reflow the tubing 52.

At the proximal end of the catheter body 12 that is received in a distal end of the control handle, the proximal and distal portions 35A, 36A, 35B, 36B, 35C, 36C which have extended longitudinally along the catheter shaft 12 between the second layer 23 and the third layer 24 enter the interior of the control handle 16 for connection to a printed circuit board for processing, including, for example, amplification, as known in the art.

Figure 4A:
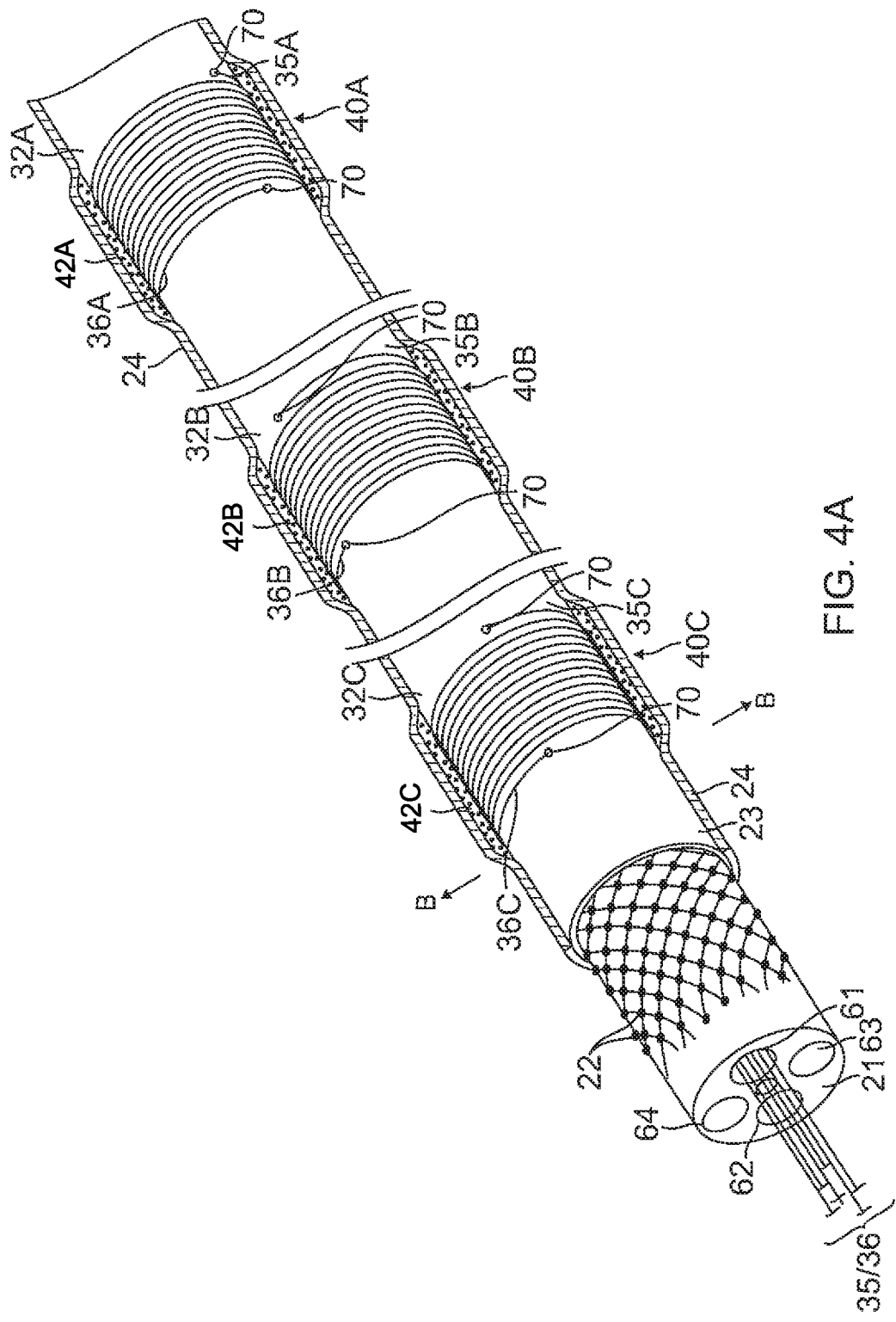
FIG. 4A is a side view of a catheter tubing, with parts broken away, in accordance with another embodiment of the present invention.
Figure 4B:
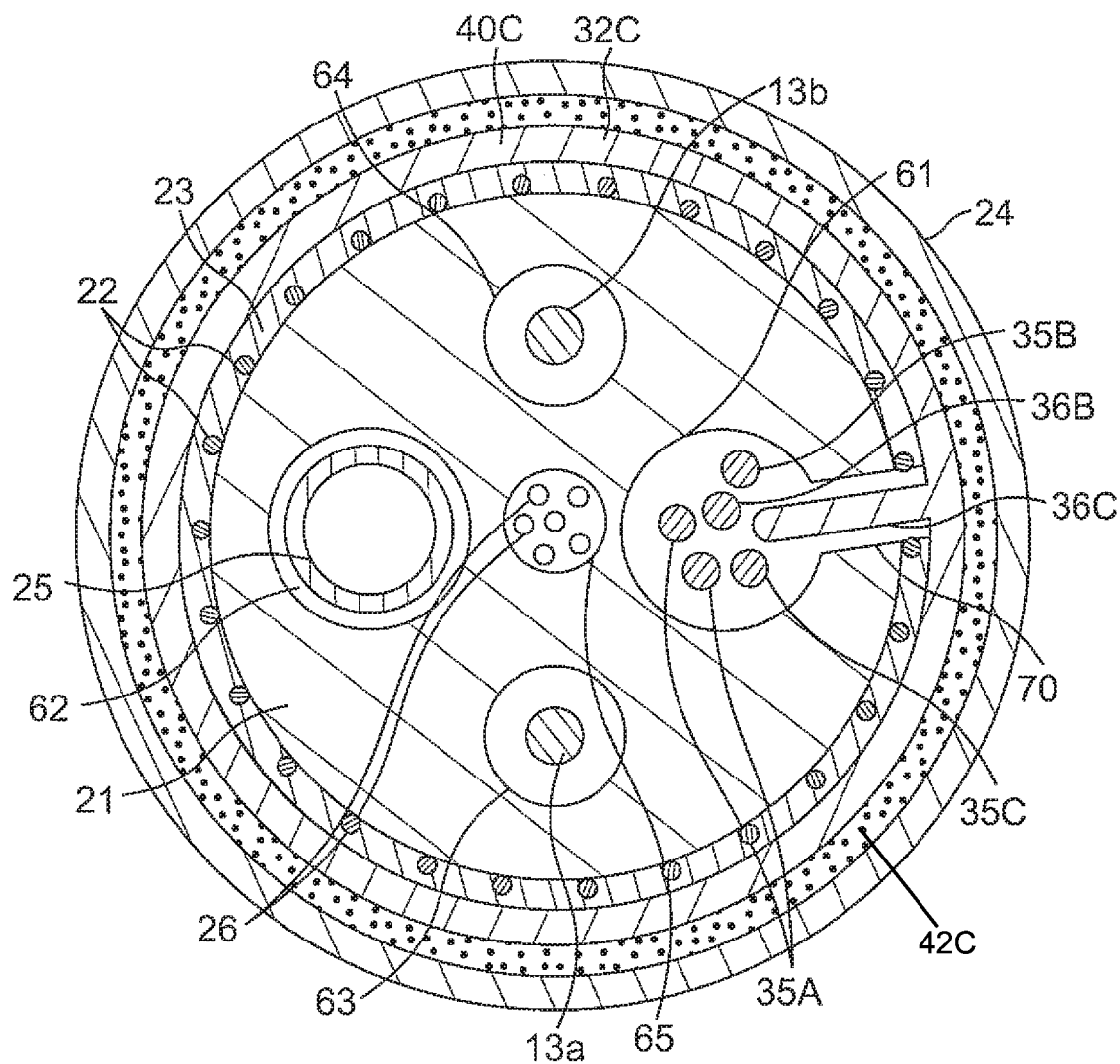
FIG. 4B is an end cross-sectional view of the catheter tubing of FIG. 4B, taken along line B-B.

In other embodiments of the present invention, the wire distal and proximal portions 35A, 36A, 35B, 36B, 35C, 36C of each coil 32A, 32B and 32C may extend proximally through a lumen 61 of the catheter shaft, as shown in FIG. 4A and FIG. 4B. A through-hole 70 is formed into the lumen through the sidewall of the catheter shaft portion (through the first layer 21, the braided mesh 22 and the second layer 23) for each wire portion 35A, 36A, 35B, 36B, 35C and 36C.

As such, sleeves 38B and 38C are not needed. As shown in FIG. 4A, the extruded first layer 21 may be formed as a multi-lumened tubing with lumens 50, 51, 52 and 53 (with use of one or more suitable mandrels). The through-hole 70 may be formed to communicate with the lumen 61, such that the wire portions 35A, 36A, 35B, 36B, 35C and 36C all pass through the dedicated lumen 61 along the length of the catheter shaft.

In some embodiments, lumen 62 may be provided for irrigation tubing 25 and lumen 65 may be provided for tip electrode lead wires 26. Diametrically opposing lumens 63 and 64 may be suitable for a pair of puller wires 13a and 13b to provide the catheter with bi-directional deflection. In that regard, the shaft portion 11 with the one or more embedded SAS in its layered construction is suitable as segment of the deflection portion 14 (as shown in FIG. 1), for example, that extends distal of a single lumened catheter body through which the pair of puller wires extends. Each puller wire has a proximal end anchored in the control handle 16 and a distal end anchored at or near a distal end of the deflection portion 14. Surrounding each puller wire is a compression coil (now shown) having a proximal end at a proximal end of the catheter body, and a distal end at or near a proximal end of the deflection portion 14, as known in the art and understood by one of ordinary skill in the art.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. It is understood that a feature of the present invention is applicable to multiplying linear motion of a puller wire, contraction wire, or any other object requiring insertion, removal, or tensioning within a medical device, including the disclosed electrophysiology catheter. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated body having a multi-layered portion with a magnetic-based sensor assembly,
   a control handle proximal of the elongated body, and
   a distal section distal of the elongated body, the distal section having an electrode,
   wherein the multi-layered portion of the elongated body has a first layer, a braided mesh over the first layer, and a second layer, the first layer defining a lumen, the second layer having a reflowed construction over the braided mesh and the first layer, the first and second layers being of similar thermoplastic materials, and
   wherein the magnetic-based sensor assembly comprises:
      a plurality of wire sensors mounted on the second layer of the multi-layered portion of the elongated body, the plurality of wire sensors comprising:
         a first wire sensor comprising a first continuous wire with a first coil portion, a first distal portion and a first proximal portion, the first coil portion being at a first location on the second layer of the multi-layered portion of the elongated body, and the first distal portion and the first proximal portion extending toward a proximal end of the elongated body; and a second wire sensor comprising a second continuous wire with a second coil portion, a second distal portion and a second proximal portion, the second coil portion being at a second location on the second layer of the multi-layered portion of the elongated body, the second location being distal of the first location, and the second distal portion and the second proximal portion extending toward the proximal end of the elongated body; and a first insulation sleeve mounted in circumferential surrounding relation on the second layer of the multi-layered portion of the elongated body, the first coil portion being mounted on the first insulation sleeve, and the second distal portion and the second proximal portion of the second wire sensor passing underneath the first coil portion between the first insulation sleeve and the second layer of the multi-layered portion of the elongated body.

2. The catheter of claim 1, wherein the plurality of wire sensors further comprises a third wire sensor comprising a third continuous wire with a third coil portion, a third distal portion and a third proximal portion, the third coil portion being at a third location on the second layer of the multi-layered portion of the elongated body, the third location being distal of the first and second locations, and the third distal portion and the third proximal portion extending toward the proximal end of the elongated body.

3. The catheter of claim 2, wherein the third distal portion and the third proximal portion of the third wire sensor extend proximally past the first coil portion of the first wire sensor and the second coil portion of the second wire sensor.

4. The catheter of claim 2, wherein the elongated body has a third layer covering the first, second and third wire sensors.

5. The catheter of claim 2, wherein the third distal portion and the third proximal portion of the third wire sensor extend toward the proximal end of the elongated body, with one segment of each of the third distal portion and the third proximal portion of the third wire sensor passing under the first coil portion of the first wire sensor and another segment of each of the third distal portion and the third proximal portion of the third wire sensor passing under the second coil portion of the second wire sensor.

6. The catheter of claim 2, wherein the magnetic-based sensor assembly further comprises a second insulation sleeve mounted in circumferential surrounding relation on the second layer of the multi-layered portion of the elongated body, the second coil portion being mounted on the second insulation sleeve, and the third distal portion and the third proximal portion of the third wire sensor each having a first segment passing underneath the first coil portion between the first insulation sleeve and the second layer of the multi-layered portion of the elongated body and a second segment passing underneath the second coil portion between the second insulation sleeve and the second layer of the multi-layered portion of the elongated body.

7. The catheter according to claim 6, wherein the magnetic-based sensor assembly further comprises:

a first encapsulation coating circumferentially surrounding the first coil portion of the first wire sensor on the second layer of the multi-layered portion of the elongated body;

a second encapsulation coating circumferentially surrounding the second coil portion of the second wire sensor on the second layer of the multi-layered portion of the elongated body; and a third encapsulation coating circumferentially surrounding the third coil portion of the third wire sensor on the second layer of the multi-layered portion of the elongated body.

8. The catheter according to claim 7, further comprising a third layer extending over the magnetic-based sensor assembly such that the third layer encases each of the first, second and third encapsulation coatings and each of the first, second and third wire sensors.

9. The catheter of claim 1, wherein the elongated body has a third layer covering the multi-layered portion of the elongated body with the magnetic-based sensor assembly.

10. The catheter of claim 1, wherein the multi-layered portion of the elongated body with the magnetic-based sensor assembly has a single central lumen.

11. The catheter of claim 1, wherein the multi-layered portion of the elongated body with the magnetic-based sensor assembly has a plurality of lumens.

12. The catheter of claim 1, wherein the magnetic-based sensor assembly further comprises a respective encapsulation coating for each of the plurality of wire sensors, the respective encapsulation coating surrounding a respective coil portion of its respective wire sensor on the second layer of the multi-layered portion of the elongated body.

13. The catheter of claim 12, further comprising a third layer extending over the magnetic-based sensor assembly such that the third layer encases each of the respective encapsulation coatings and the plurality of wire sensors.

14. A method of manufacturing the catheter of claim 1, comprising:
extruding the first layer;
placing the braided mesh on the first layer;
placing a first heat shrink tubing as the second layer over the braided mesh and the first layer; and
heating the first heat shrink tubing to reflow the second layer over the braided mesh and the first layer.

15. The method of claim 14, further comprising:
placing a second heat shrink tubing over the first coil portion of the first wire sensor; and
heating the second heat shrink tubing to form a seal over the first coil portion of the first wire sensor.

16. A method of manufacturing the catheter of claim 1, comprising:
extruding the first layer;
placing the braided mesh on the first layer;
placing a first heat shrink tubing as the second layer over the braided mesh and the first layer;
heating the first heat shrink tubing to a temperature within the overlapping temperature ranges of the first and second thermoplastic materials; and
wrapping the first wire sensor on the second layer.

17. The method of claim 16, further comprising supporting the first layer with a mandrel that remains with the first layer during the wrapping the first wire sensor on the second layer.

18. A method of manufacturing the catheter of claim 1, comprising:
extruding the first layer;
placing the braided mesh on the first layer;
placing a first heat shrink tubing over the braided mesh and the first layer;
heating the first heat shrink tubing to a temperature to sufficiently melt the first and second layers to adhere to each other;
placing the first insulation sleeve on the second layer; and wrapping each wire sensor on the second layer with a mandrel supporting the first layer, the braided mesh and the second layer.

19. The method of claim 18, further comprising:

placing a second heat shrink tubing as a third layer over each wire sensor; and heating the second heat shrink tubing to seal each wire sensor on the elongated body.

20. The method of claim 19, further comprising injecting epoxy through the second heat shrink tubing to encase each wire sensor.

* * * * *